United States Patent
Royer et al.

(10) Patent No.: US 11,661,416 B2
(45) Date of Patent: May 30, 2023

(54) METHOD FOR ISOLATION OF A DIANHYDRIDE AND DIANHYDRIDES PREPARED BY THE METHOD

(71) Applicant: SABIC GLOBAL TECHNOLOGIES B.V., Bergen op Zoom (NL)

(72) Inventors: Aaron Matthew Royer, Mt. Vernon, IN (US); Sivakumar Periyasamy, Bangalore (IN); Ravi Gautam, Bangalore (IN); Jorge Jimenez Umana, Sugar Land, TX (US); Gregory L. Hemmer, Mt. Vernon, IN (US); Robert Werling, Mount Vernon, IN (US); Hareesh Shamrao Deshpande, Bangalore (IN)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 191 days.

(21) Appl. No.: 17/049,601

(22) PCT Filed: May 13, 2019

(86) PCT No.: PCT/US2019/031972
§ 371 (c)(1),
(2) Date: Oct. 22, 2020

(87) PCT Pub. No.: WO2019/222077
PCT Pub. Date: Nov. 21, 2019

(65) Prior Publication Data
US 2021/0246124 A1    Aug. 12, 2021

(30) Foreign Application Priority Data
May 14, 2018    (EP) .................................... 18172207

(51) Int. Cl.
*C07D 405/12*    (2006.01)
*C07D 407/12*    (2006.01)

(52) U.S. Cl.
CPC ......... *C07D 405/12* (2013.01); *C07D 407/12* (2013.01)

(58) Field of Classification Search
CPC .................................................... C07D 405/12
USPC ........................................................ 549/250
See application file for complete search history.

(56) References Cited

U.S. PATENT DOCUMENTS

| | | |
|---|---|---|
| 3,389,970 A | 6/1968 | Scheibel |
| 3,875,116 A | 4/1975 | Heath et al. |
| 3,956,320 A | 5/1976 | Heath et al. |
| 4,020,089 A | 4/1977 | Markezich |
| 4,116,980 A | 9/1978 | Webb |
| 4,217,281 A | 8/1980 | Markezich et al. |
| 4,257,953 A | 3/1981 | Williams, III et al. |
| 4,318,857 A | 3/1982 | Webb et al. |
| 4,329,291 A | 5/1982 | Webb et al. |
| 4,329,292 A | 5/1982 | Webb |
| 4,329,496 A | 5/1982 | Webb |
| 4,340,545 A | 7/1982 | Webb et al. |
| 4,417,044 A | 11/1983 | Parekh |
| 4,520,204 A | 5/1985 | Evans |
| 4,571,425 A | 2/1986 | Silva |
| 4,584,388 A | 4/1986 | Webb |
| 4,902,809 A | 2/1990 | Groeneweg et al. |
| 5,359,084 A | 10/1994 | Dellacoletta et al. |
| 6,008,374 A | 12/1999 | Dellacoletta et al. |
| 6,235,866 B1 | 5/2001 | Khouri et al. |
| 6,265,521 B1 | 7/2001 | Fyvie et al. |
| 6,498,224 B1 | 12/2002 | Odle et al. |
| 7,153,394 B2 | 12/2006 | Guggenheim et al. |
| 10,407,397 B2 * | 9/2019 | Royer .................. C07D 307/89 |
| 2006/0205958 A1 | 9/2006 | Brunelle et al. |
| 2009/0056793 A1 | 3/2009 | Langhals et al. |
| 2009/0247727 A1 | 10/2009 | Bernabe et al. |

(Continued)

FOREIGN PATENT DOCUMENTS

| | | |
|---|---|---|
| DE | 3213166 A1 | 10/1983 |
| EP | 0477539 A1 | 4/1992 |

(Continued)

OTHER PUBLICATIONS

Basosca, I. et al., "Comparative study of polyimides containing different flexible linkages", J. Iran Chem. Soc., vol. 9, 2012; pp. 901-910.
Bruma, M. et al., "Polyetherimides for Gas Separation Membranes", Molecular Crystals and Liquid Crystals, vol. 418, pp. 11-19.
Hu, Yu Lin et al., "An inexpensive and efficient synthetic method for the preparation of pyromellitic dianhydride promoted by ionic liquid", ARKIVOC, vol. 9, 2010; pp. 63-74.
International Search Report for International Application No. PCT/US2017/028263; International Filing Date: Apr. 19, 2017; dated Aug. 24, 2017; 6 pages.
International Search Report for the corresponding International Application No. PCT/US2019/030810; International Filing Date: May 6, 2019; dated Jul. 30, 2019. 5 pages.

(Continued)

*Primary Examiner* — Kahsay Habte
(74) *Attorney, Agent, or Firm* — Cantor Colburn LLP (57) ABSTRACT

A method for producing an aromatic dianhydride includes reacting an aromatic diimide with a substituted or unsubstituted phthalic anhydride in an aqueous medium in the presence of an amine exchange catalyst to provide an aqueous reaction mixture including an N-substituted phthalimide, an aromatic tetraacid salt, and at least one of an aromatic triacid salt and an aromatic imide diacid salt. The method further includes removing the phthalimide from the aqueous reaction mixture by extracting the aqueous reaction mixture with an organic solvent in a first extractor for a first time period, at a first extraction temperature and subsequent to the first time period, extracting the aqueous reaction mixture with an organic solvent in a second extractor for a second time period, at a second extraction temperature. The aromatic tetraacid salt is converted to the corresponding aromatic dianhydride. Aromatic dianhydrides prepared according to the method are also described.

11 Claims, 2 Drawing Sheets

(56) References Cited

U.S. PATENT DOCUMENTS

| | | |
|---|---|---|
| 2011/0319620 A1 | 12/2011 | Ishihara et al. |
| 2019/0040201 A1 | 2/2019 | Patil et al. |
| 2019/0092726 A1 | 3/2019 | Schulte, II et al. |
| 2019/0119240 A1 | 4/2019 | Royer et al. |
| 2019/0135750 A1 | 5/2019 | Croll et al. |

FOREIGN PATENT DOCUMENTS

| | | |
|---|---|---|
| WO | 2017172593 A1 | 5/2017 |
| WO | 2017189293 A1 | 11/2017 |

OTHER PUBLICATIONS

Pinzow, Leonard, "Characteristics of a pulsed packed, liquid-liquid extraction column", Calhoun: The NPS Institutional Archive, Retrieved from the Internet on Sep. 20, 2018; http://hdl.handle.net/10945/13989; Jan. 1, 1957; pp. 1-105.

Rauber, Johannes, "Design Practice for Packed Liquid Liquid Extraction Columns", Sulzer, Retrieved from the Internet on Sep. 20, 2018; http://folk.ntnu.no/skoge/prost/proceedings/aiche-2006/data/papers/P73337.pdf; Jan. 1, 2006; pp. 1-12.

Schwartz, W. T., "A Novel Route to Aryl Diether Dianhydrides", High Performance Polymers, vol. 2, No. 3, 1990; pp. 189-196.

Wei, Haibing et al., "Comparative Study on Polyimides from Isomeric 3,3'-, 3,4'-, and 4,4'-Linked Bis(thioether anhydride)s", Journal of Polymer Science Part A: Polymer Chemistry, vol. 49, 2011; pp. 2484-2494.

Written Opinion for the corresponding International Application No. PCT/US2019/030810; International Filing Dtae: May 6, 2019; dated Jul. 30, 2019. 9 pages.

Written Opinion of the International Searching Authority for International Application No. PCT/US2017/028263; International Filing Date Apr. 19, 2017; dated Aug. 24, 2017; 9 pages.

Yoon, Chong-Bok et al., "Facile synthesis of new NLO-functionalized polyimides via Mitsunobu reaction", Journal Material Chemistry, vol. 9; 1999; pp. 2339-2344.

International Search Report for the corresponding International Application No. PCT/US2019/035325; International Filing Date: Jun. 4, 2019; dated Jul. 24, 2019. 6 pages.

Written Opinion for the corresponding International Application No. PCT/US2019/035325; International Filing Date: Jun. 4, 2019; dated Jul. 24, 2019. 6 pages.

International Search Report for International Application No. PCT/US2019/031972; International Filing Date: May 13, 2019; dated Jul. 8, 2019; 8 pages.

Written Opinion for International Application No. PCT/US2019/031972; International Filing Date: May 13, 2019; dated Jul. 8, 2019; 12 pages.

International Search Report for International Application No. PCT/US2019/037182; International Filing Date: Jun. 14, 2019; dated Aug. 26, 2019; 6 pages.

Written Opinion for International Application No. PCT/US2019/037182; International Filing Date Jun. 14, 2019; dated Aug. 26, 2019; 9 pages.

* cited by examiner

METHOD FOR ISOLATION OF A DIANHYDRIDE AND DIANHYDRIDES PREPARED BY THE METHOD

CROSS-REFERENCE TO RELATED APPLICATIONS

This application is a National Stage application of PCT/US2019/031972, filed May 13, 2019, which claims benefit of European Application No. 18172207.5 filed on May 14, 2018, both of which are incorporated by reference herein in their entirety.

BACKGROUND

Polyetherimides are a class of high performance polymers that can be processed to make molded articles, fibers, films, foams, and the like. Polyetherimides further have high strength, toughness, heat resistance, modulus, and broad chemical resistance, and so are widely used in industries as diverse as automotive, telecommunication, aerospace, electrical/electronics, transportation, and healthcare. Polyetherimides have shown versatility in various manufacturing processes, proving amenable to techniques including injection molding, extrusion, and thermoforming, to prepare various articles.

A number of processes for making polyetherimides have been disclosed. Two processes which have been of particular interest are the so-called melt polymerization and solution polymerization processes. Solution polymerization is generally conducted by reacting an aromatic dianhydride and an organic diamine in an inert solvent at elevated temperatures to form an amide-acid polymer via ring opening of the anhydride by nucleophilic attack of the diamine. The polyamide-acid is then formed into a polyetherimide by removal of water, for example by azeotropic distillation.

Aromatic dianhydrides are thus important to the production of polyetherimides. The aromatic dianhydrides can be prepared using an exchange reaction between an aromatic bisimide and a substituted or unsubstituted phthalic anhydride. In addition to dianhydride, the exchange reaction often produces various by-products which result in decreased yields of the dianhydride.

Accordingly, there remains a need for an improved method for producing and isolating dianhydrides that can provide high yields and minimize by-product formation

BRIEF DESCRIPTION

A method for producing an aromatic dianhydride comprises reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 150 to 300 psig (1.13 to 2.16 MPa), preferably 200 to 250 psig (1.48 to 1.82 MPa); removing the N-substituted phthalimide from the aqueous reaction mixture by extracting the aqueous reaction mixture with an organic solvent in a first extractor, for a first time period, at a first extraction temperature that is 60 to 160° C., provided that the first extraction temperature is at least 10° C., preferably at least 20° C. or more preferably at least 30° C., or most preferably at least 40° C. lower than a maximum of the reaction temperature; subsequent to the first time period, extracting the aqueous reaction mixture with an organic solvent in a second extractor, for a second time period, at a second extraction temperature that is 120 to 250° C., provided that the second extraction temperature is at least 5° C., preferably at least 10° C., more preferably at least 20° C. higher than the first extraction temperature; and converting the aromatic tetraacid salt to the corresponding aromatic dianhydride; wherein the aqueous reaction mixture has a solids content of greater than 16.5 wt %; and wherein extracting in the first extractor and the second extractor uses a column configuration wherein the organic solvent provided to the first extractor and the second extractor simultaneously is fresh organic solvent and the organic solvent is provided to the first and second extractors in a volumetric ratio of the organic solvent to the aqueous medium is greater than or equal to 0.5:1; or the organic solvent provided to the second extractor is fresh organic solvent and the organic solvent from the second extractor is fed to the first extractor and the organic solvent is provided to the second extractor in a volumetric ratio of the organic solvent to the aqueous medium is 0.5:1 to 1.5:1.

An aromatic dianhydride prepared by the method has an imide anhydride content of 2 weight percent or less.

BRIEF DESCRIPTION OF THE DRAWINGS

The following figures represent exemplary embodiments.

DETAILED DESCRIPTION

The present inventors have discovered that use of a modified extraction procedure for isolation of an aromatic dianhydride can increase the overall dianhydride conversion and yield. In particular, the extraction procedure of the present disclosure includes two extractors wherein each extraction is conducted at a particular temperature. The present inventors have unexpectedly discovered that use of high solids content and a particular column configuration can be especially advantageous for achieving high overall dianhydride conversion and yield. The isolated aromatic dianhydrides advantageously have reduced amounts of imide anhydride by-products, which can facilitate production of high molecular weight poly(etherimide).

Accordingly, a method for producing an aromatic dianhydride represents an aspect of the present disclosure. The method comprises reacting an aromatic diimide (also referred to as an "aromatic bisimide" or "bisimide") with a substituted or unsubstituted phthalic anhydride in an aqueous medium in the presence of an amine exchange catalyst and under conditions effective to provide an aqueous reaction mixture.

The aromatic bisimide can be of the formula (1)

wherein T is —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing. In an aspect, the R$^1$ is a monovalent C$_1$-13 organic group.

In an aspect, T is —O— or a group of the formula —O—Z—O— wherein the divalent bonds of the —O— or the —O—Z—O— group are in the 3,3', 3,4', 4,3', or the 4,4' positions. Exemplary groups Z include groups of formula (2)

wherein R$^a$ and R$^b$ are each independently the same or different, and are a halogen atom or a monovalent C$_{1-6}$ alkyl group, for example; p and q are each independently integers of 0 to 4; c is 0 to 4; and X is a bridging group connecting the hydroxy-substituted aromatic groups, where the bridging group and the hydroxy substituent of each C$_6$ arylene group are disposed ortho, meta, or para (specifically para) to each other on the C$_6$ arylene group. The bridging group X$^a$ can be a single bond, —O—, —S—, —S(O)—, —S(O)$_2$—, —C(O)—, or a C$_{1-18}$ organic bridging group. The C$_{1-18}$ organic bridging group can be cyclic or acyclic, aromatic or non-aromatic, and can further comprise heteroatoms such as halogens, oxygen, nitrogen, sulfur, silicon, or phosphorous. The C$_{1-18}$ organic group can be disposed such that the C$_6$ arylene groups connected thereto are each connected to a common alkylidene carbon or to different carbons of the C$_{1-18}$ organic bridging group. A specific example of a group Z is a divalent group of the formula (3a) or (3b)

wherein Q is —O—, —S—, —C(O)—, —SO$_2$—, —SO—, —P(R$^a$)(=O)— wherein R$^a$ is a C$_{1-8}$ alkyl or C$_{6-12}$ aryl, or —C$_y$H$_{2y}$— wherein y is an integer from 1 to 5 or a halogenated derivative thereof (including a perfluoroalkylene group). Exemplary dihydroxy aromatic compounds from which Z can be derived include but are not limited to 2,2-bis(2-hydroxyphenyl)propane, 2,4'-dihydroxydiphenylmethane, bis(2-hydroxyphenyl)methane, 2,2-bis-(4-hydroxyphenyl)propane ("bisphenol A" or "BPA"), 1,1-bis-(4-hydroxyphenyl)ethane, 1,1-bis-(4-hydroxyphenyl)propane, 2,2-bis-(4-hydroxyphenyl)pentane, 3,3-bis-(4-hydroxyphenyl)pentane, 4,4'-dihydroxybiphenyl, 4,4'-dihydroxy-3,3,5,5'-tetramethylbiphenyl, 2,4'-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenylsulfide, hydroquinone, resorcinol, 3,4-dihydroxydiphenylmethane, 4,4'-dihydroxybenzophenone, 4,4'-dihydroxydiphenylether, and the like, or a combination comprising at least one of the foregoing. In an aspect, Z is derived from bisphenol A, such that Q in the above formula is, 2,2-isopropylidene. Thus in an aspect, Z is 2,2-(4-phenylene) isopropylidene. In an aspect, R$^1$ is a C$_{1-4}$ alkyl group, for example a methyl group, an ethyl group, a propyl group, or a butyl group, preferably a methyl group.

In an aspect, the aromatic bisimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing.

The substituted or unsubstituted phthalic anhydride can be of the formula (4)

wherein X is fluoro, chloro, bromo, iodo, nitro, or a combination comprising at least one of the foregoing, and n is 0 or 1. In an aspect, n is 0 and the phthalic anhydride is an unsubstituted phthalic anhydride. In an aspect, n is 1, and the phthalic anhydride is a substituted phthalic anhydride, wherein X is fluoro, chloro, bromo, iodo, nitro, or a combination comprising at least one of the foregoing. In an aspect, the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing. Specific examples of suitable halophthalic anhydrides include 3-fluorophthalic anhydride, 4-fluorophthalic anhydride, 3-chlorophthalic anhydride, 4-chlorophthalic anhydride, 3-bromophthalic anhydride, 4-bromophthalic anhydride, 3-iodophthalic anhydride, and 4-iodophthalic anhydride. In an aspect, the substituted or unsubstituted phthalic anhydride is preferably phthalic anhydride.

Reacting the aromatic bisimide with the substituted or unsubstituted phthalic anhydride is carried out in aqueous medium in the presence of an amine exchange catalyst. The amine exchange catalyst can include a (C$_{1-20}$ alkyl)-substituted amine, preferably a tri(C$_{1-20}$ alkyl)amine. In an aspect, the amine exchange catalyst is preferably triethylamine trimethylamine, or a combination comprising at least one of the foregoing. In an aspect, the initial molar ratio of amine exchange catalyst to the phthalic anhydride is 1:1 to 2:1.

The reacting is further carried out under conditions effective to provide an aqueous reaction mixture. Effective conditions can include reacting at a reaction temperature that is 140 to 250° C., for example 160 to 200° C., and a reaction pressure of 150 to 300 psig (1.13 to 2.16 megapascals (MPa)), preferably 200 to 250 psig (1.48 to 1.82 MPa), more preferably 200 to 230 psig (1.48 to 1.68 MPa).

In an aspect, the initial molar ratio of phthalic anhydride to aromatic bisimide is 4:1 to 20:1, or 4:1 to 10:1, or 4:1 to 8:1, or 4:1 to 5.5:1, or 4:1 to 5.5:1. Without wishing to be bound by theory, it is believed that a molar ratio of phthalic anhydride to aromatic bisimide of 4:1 to 5:1 is preferred at least for economic reasons.

The aqueous reaction mixture provided by reacting the aromatic bisimide with the substituted or unsubstituted phthalic anhydride comprises an N-substituted phthalimide, an aromatic tetraacid salt, and at least one of an aromatic triacid salt and an aromatic imide diacid salt.

In an aspect, the aromatic tetra acid salt is of the formula (5)

the aromatic triacid salt is of the formula (6)

and
the aromatic imide-diacid salt is of the formula (7)

wherein T can be as described above, and is preferably —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 Ca alkyl groups, 1 to 8 halogen atoms, or a combination comprising at least one of the foregoing, R$^1$ is a C$_{1-13}$ organic group, or a C$_{1-4}$ alkyl group, preferably a methyl group, and Y is a cationic group, preferably a C$_{1-20}$ trialkylammonium group (i.e., an aromatic tetraacid ammonium salt, triacid ammonium salt, and imide diacid ammonium salt), or a proton (i.e., the aromatic tetraacid ammonium salt, triacid ammonium salt, and imide diacid ammonium salt can be in the form of the corresponding aromatic tetraacid, triacid, and imide acid, respectively). In an aspect, Y is a C$_{1-20}$ trialkylammonium group, preferably a triethylammonium group. Thus, in an aspect, the aromatic tetra acid salt can be an aromatic tetra acid triethylamine salt, the aromatic triacid salt can be an aromatic triacid triethylamine salt, and the aromatic imide-diacid salt can be an aromatic imide-diacid triethylamine salt. In an aspect, T is —O—Z—O—, wherein Z is derived from bisphenol A.

The divalent bonds of the —O—Z—O— group are in the 3,3', 3,4', 4,3', or the 4,4' positions.

In an aspect, the aqueous reaction mixture can further comprise at least one of the aromatic bisimide and the substituted or unsubstituted phthalic anhydride. In an aspect, the aqueous reaction mixture can further comprise the substituted or unsubstituted phthalic anhydride, preferably wherein the substituted or unsubstituted phthalic anhydride is in the form of the corresponding ring-opened diacid salt, for example a corresponding ring-opened diacid C$_{1-20}$ trialkylammonium salt.

The method further comprises removing the N-substituted phthalimide and any residual aromatic bisimide from the aqueous reaction mixture by extracting the aqueous reaction mixture with an organic solvent. In an aspect, the organic solvent is a (C$_{1-6}$ alkyl)benzene, benzene, or a halogenated aromatic solvent. For example, the organic solvent can comprise toluene, xylene, chlorobenzene, ortho-dichlorobenzene, or a combination comprising at least one of the foregoing. In an aspect, the organic solvent is present in a volumetric ratio of organic solvent to aqueous medium of 0.3:1 to 3:1, or 0.3:1 to 2:1, or 0.3:1 to 1.1:1, or 0.3:1 to 1:1, or 0.5:1 to 1:1, or 0.75:1 to 1:1. In an aspect, the organic solvent can optionally comprise 0 to 15 weight percent, or 1 to 10 weight percent, or 2 to 8 weight percent of a tri(C$_{1-6}$ alkyl)amine, preferably triethylamine.

The extracting to remove the N-substituted phthalimide and any residual aromatic bisimide is in a first and a second extraction column. When using an extraction column, the aqueous phase from the exchange reaction is typically fed into the top of the extraction column while the organic solution is fed into the bottom of the exchange column.

The extracting is carried out for a first period of time in a first extractor and at a first extraction temperature that is 60 to 160° C., or 60 to 150° C., provided that the first extraction temperature is at least 10° C., preferably at least 20° C., more preferably at least 30° C., most preferably at least 40° C. lower than a maximum reaction temperature. Use of the above defined first extraction temperature that is at least 10° C. lower than a maximum reaction temperature facilitates removal of the N-substituted phthalimide. Advantageously, using the method described herein, loss of conversion of aromatic bisimide to aromatic dianhydride can be reduced or eliminated.

The first period of time can be, for example, 30 seconds to 3 hours, or 5 minutes to 3 hours, or 20 minutes to 3 hours, or 20 minutes to 2 hours, or 20 minutes to 1 hour, or 1 to 3 hours, or 1 to 2 hours, or 1 to 1.5 hours, preferably 5 minutes to 3 hours, or 20 minutes to 2 hours, or 20 minutes to 1 hour In an aspect, at least 50%, at least 70%, at least 80%, or at least 90% of the N-substituted phthalimide in the aqueous reaction mixture at the beginning of the first time period can be extracted into the organic solvent at the end of the first time period.

Subsequent to the first time period, the aqueous reaction mixture can be extracted with an organic solvent for a second time period in a second extractor and at a second extraction temperature that is 120 to 250° C., or, 140 to 250° C., or 160 to 200° C., provided that the second extraction temperature is at least 5° C., preferably at least 10° C., more preferably at least 20° C. higher than the first extraction temperature. The use of the above defined second extraction temperature that is at least 5° C. higher than the first extraction temperature can provide improved conversion and ultimately higher yields for the aromatic dianhydride, particularly at a desired substituted phthalic anhydride: aromatic bisimide molar ratio and a particular solids content as defined herein.

The second period of time can be, for example, 0.5 to 3 hours, or 0.5 to 2 hours, or 0.2 to 1.5 hours. In an aspect, conversion of the aromatic bisimide to aromatic dianhydride can be greater than 70%, or greater than 75%, or greater than 78% or greater than 80% at the end of the second time period. In an aspect, conversion of the aromatic bisimide to aromatic dianhydride can be 70 to 95%, or 75 to 90%, or 78 to 90%, or 80 to 90%, or 80 to 95% at the end of the second time period.

Figure 3:
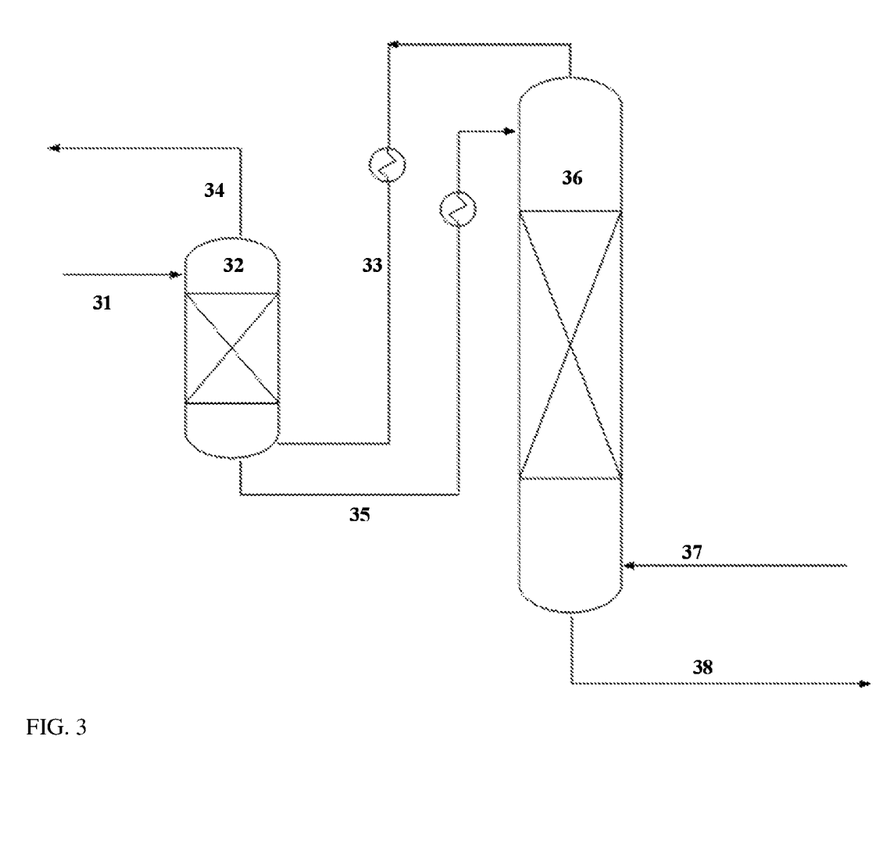
FIG. 3 shows a schematic illustration of a column configuration according to the present disclosure.

In an aspect, the organic solvent can be provided to the second extractor to extract the aqueous reaction mixture for the second period of time and subsequently the same organic solvent from the second extractor can be used in a first extractor to extract the aqueous reaction mixture for the first period of time. For example, in a particular aspect, the organic solvent recovered from the second extractor can be fed for use in the first extractor. This is illustrated in FIG. 3. As shown in FIG. 3, the aqueous reaction mixture 31 can be fed to the cold extraction column 32. An organic solvent stream 33 is obtained from the hot extractor 36 and fed to the cold extractor. The cold extraction in the first extractor 32 provides an organic stream 34 removed from the top of the column, and an aqueous stream 35 removed from the bottom of the column, which is provided to the second, hot extractor 36. Fresh organic solvent 37 is provided to the second, hot extractor, and the hot extraction provides recovered organic stream 33, which is provided to the cold extractor 32, and aqueous outlet 38 containing the desired aromatic dianhydride product, which is removed for isolation.

Figure 2:
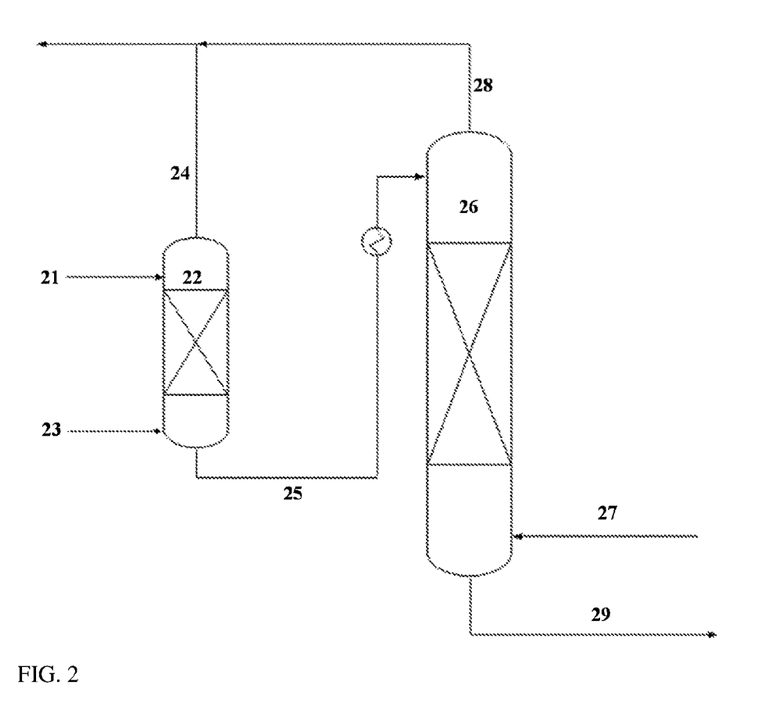
FIG. 2 shows a schematic illustration of a column configuration according to the present disclosure.

In an aspect, the organic solvent can be simultaneously provided to both extractors, such that fresh organic solvent is used for each extraction. This is illustrated in FIG. 2. As shown in FIG. 2, the aqueous reaction mixture 21 is provided to the first extractor (i.e., the cold extraction column) 22. Fresh organic solvent 23 is also provided to the extractor 22. The first extractor provides an organic stream 24 removed from the top of the column and an aqueous stream 25 removed from the bottom of the column. The aqueous stream 25 is provided to a second extractor (i.e., a hot extraction column) 26. Additional fresh organic solvent 27 is also provided to the second extractor 26. The second extractor 26 provides an organic outlet stream 28 removed from the top of the column and an aqueous outlet 29 containing the desired aromatic dianhydride product, which is removed for isolation.

In an aspect, a combination of fresh organic solvent and recycled organic solvent recovered from the outlet of one or both of the first and second reactors can be used for each extraction. For example, a combination of fresh organic solvent and recycled organic solvent recovered from the outlet of the second extractor and used in the first extractor can be used.

In an aspect, the extracting for the first time period can be in a first extractor and the extracting for the second period of time can be in a second extractor, and the organic solvent is fresh organic solvent provided to the first extractor and the second extractor simultaneously and the organic solvent is provided to the first and second extractors in a volumetric ratio of the organic solvent to the aqueous medium is greater than or equal to 0.5:1.

In another aspect, the extracting for the first time period can be in a first extractor and the extracting for the second period of time can be in a second extractor, and the organic solvent provided to the second extractor is fresh organic solvent and the organic solvent from the second extractor is fed to the first extractor and the organic solvent is provided to the second extractor in a volumetric ratio of the organic solvent to the aqueous medium is 0.5:1 to 1.5:1, or 0.9:1 to 1.2:1.

In an aspect, the extracting provides an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing, and an organic stream comprising the organic solvent, N-substituted phthalimide, and optionally any residual aromatic bisimide.

In an aspect, the method can further include repeating the extracting to provide conversion of the aromatic bisimide to aromatic dianhydride tetra acid salt at the end of the second time period in order to provide the desired conversion, for example greater than 70%, or greater than 75%, or greater than 78%, or greater than 80%. Repeating the extracting can include any number of additional extractions at either the first temperature or the second temperature, and in any order. For example, in an aspect, the method can further comprise repeating the extracting for a first period of time and at a first extraction temperature. In an aspect, the method can further comprise repeating the extracting for a first period of time and at a first extraction temperature, and subsequently repeating the extracting for a second period of time and at a second extraction temperature. In an aspect, the process of the present disclosure can provide a sufficiently high first pass conversion to dianhydride (e.g., after the first and second extractions), and no further extractions are needed.

The method further comprises converting the aromatic tetraacid salt to the corresponding aromatic dianhydride. The amount of time as well as the temperature for the converting is generally dependent upon the identity of the dianhydride and can be readily determined by one of ordinary skill in the art. For example, useful temperatures can be 160 to 300° C., or 180 to 240° C. or 200 to 220° C. The conversion of the aromatic tetraacid salt to dianhydride is a cyclization with the concurrent formation of water and evolution of a free amine species derived from the cationic group Y. For example, the tetraacid salt can be condensed by refluxing in the presence of a dehydrating agent, for example acetic anhydride. In an aspect, a temperature of 100 to 225° C. and a pressure of 0 to 1 MPa can be used. It is also noted that any phthalic anhydride present in the form of the corresponding ring-opened diacid salt present can be converted to phthalic anhydride by cyclization with the concurrent formation of water and evolution of a free amine species derived from the cationic group under the same conditions described above for the conversion of the aromatic tetraacid salt. Advantageously, trace water, catalyst, and other residual volatile materials such as phthalic anhydride can also be removed as vapor under the conditions utilized for conversion. In an aspect, the converting can provide a product mixture comprising the aromatic dianhydride and an aromatic imide-anhydride, for example formed from the cyclization of the above-described aromatic triacid salt. As further discussed below, operating at the solids content described herein advantageously allows for a significant reduction in the amount of water used in the process, which ultimately requires less energy for the conversion of the extraction column effluent to the dianhydride. Thus the process described herein can offer a significant economic advantage compared to prior processes, where operating at such high solids content would not have been an obvious choice.

In an aspect, the aqueous reaction mixture can have a solids content of greater than 16.5 wt %, or greater than 17 wt %, or greater than 17.5 wt %, or 16.5 to 24 wt %, or 17 to 24 wt %, or 17.5 to 24 wt %, or 18 to 24 wt %, or 18.5 to 24 wt %, or 18.5 to 23 wt %, or 19 to 24 wt %, or 19 to 23 wt %. As used herein, the term "solids content" is defined as the weight of the aromatic bisimide, the aromatic dianhydride, and, when present, the aromatic imide-anhydride, the aromatic tetra acid salt, the aromatic triacid salt, the aromatic imide-diacid salt, and the corresponding ring-closed derivatives thereof, relative to the total weight of the reaction mixture. Advantageously, when using the solids content described herein, the process can use reduced amounts of water compared to prior processes. Thus the presently disclosed process can advantageously be a more sustainable and economically viable process.

The aromatic dianhydride can be of the formula (8)

(8)

wherein T can be as defined above. In an aspect, T is —O—Z—O—, preferably wherein Z is derived from bisphenol A (i.e., Z is 2,2-(4-phenylene)isopropylidene). Illustrative examples of aromatic dianhydrides include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride.

The aromatic imide-anhydride can be of the formula (9)

(9)

wherein T and $R^1$ are as defined above. In an aspect, T is —O—Z—O—, wherein Z is derived from bisphenol A. In an aspect, $R^1$ is preferably a methyl group.

The above-described method can be carried out as a batchwise method or a continuous method.

In an aspect, the method comprises reacting an aromatic bisimide with a substituted or unsubstituted phthalic anhydride in an aqueous medium in the presence of an amine exchange catalyst at a reaction temperature that is 160 to 270° C., or 160 to 250° C., 160 to 200° C. to form an aqueous reaction mixture; removing the N-substituted phthalimide from the aqueous reaction mixture by extracting with an organic solvent at a first extraction temperature of 60 to 150° C., and subsequently extracting the aqueous reaction mixture with an organic solvent at a second extraction temperature that is 160 to 200° C.

An aromatic dianhydride prepared according to the above-described method is another aspect of the present disclosure. The aromatic dianhydride can be of formula (8) above. Advantageously, the aromatic dianhydride can have an imide anhydride content of less than 2 weight percent, based on the total weight of the aromatic dianhydride. This is a particularly advantageous feature of the present disclosure because imide anhydride is a monofunctional reactant from the standpoint of a polymerization to form poly(etherimide). Thus, any imide anhydride present will act as a chain stopper during a polymerization reaction, making it difficult to achieve high molecular weight poly(etherimide). High molecular weight poly(etherimide) can provide many advantages, thus providing a higher purity aromatic dianhydride which in particular includes very low amounts of imide anhydride chain stopper is especially advantageous.

An improved method for isolation of an aromatic dianhydride is provided herein. The method advantageously employs extracting at carefully selected extraction conditions in order to increase overall conversion of aromatic diimide to dianhydride and increase the yield of the isolated aromatic dianhydride. Therefore, a substantial improvement in methods of isolating an aromatic dianhydride is provided.

This disclosure is further illustrated by the following examples, which are non-limiting.

EXAMPLES

The following experiments were conducted to study the effect of various process parameters on the efficiency of separating N-methylphthalimide and 4,4'-bisphenol A-bis-N-methylphthalimide (which can also include small amounts of 3,4'-bisphenol A-bis-N-methylphthalimide and 3,3'-bisphenol A-bis-N-methylphthalimide) from 4,4'-bisphenol A dianhydride. For simplicity of the discussion that follows, "N-methylphthalimide" will be referred to as "PI", the "4,4'-bisphenol A-bis-N-methylphthalimide" mixture will be referred to as "BI", and the "4,4'-bisphenol A dianhydride" product will be referred to as "DA".

Effect of Solid Content

Experiments were conducted with varying the solid content of the aqueous reaction mixture, and keeping other parameters constant. Reaction of BI to phthalic anhydride ("PA") was conducted at a BI:PA molar ratio of 1:5 at a temperature of 175° C. and an agitation speed of 300 rotations per minute (rpm). The reaction was conducted in the presence of a triethylamine (TEA) exchange catalyst. The molar ratio of phthalic anhydride to triethylamine (PA:TEA) was maintained at 1:1.5. Water was used as the solvent to provide an aqueous reaction mixture. At solids contents of 14-15 wt %, the resulting reaction outlet composition was as follows: 6.43 wt % of PI, 14.6 wt % of PA, 9.0 wt % of DA, 4.56 wt % of the corresponding imide anhydride ("IA"), 0.923 wt % BI, 43.8 wt % water, and 20.73 wt % triethylamine, wherein weight percent of each component is based on the total weight of the aqueous reaction mixture. At a solids content of 19-20 wt %, the resulting reaction outlet composition was as follows: 8.93 wt % of PI, 19.34 wt % of PA, 12.475 wt % of DA, 5.78 wt % of the corresponding imide anhydride ("IA"), 0.907 wt % BI, 25 wt % water, and 27.57 wt % triethylamine, wherein weight percent of each component is based on the total weight of the aqueous reaction mixture A comparative example was conducted at a solids content of 15 wt %. Two examples using higher solids contents of 20 wt % and 23 wt % were tested for comparison. It was observed that at 15 wt % solids, it takes approximately 50 minutes to reach equilibrium exchange. Surprisingly, when the percent solids was increased to 20 wt %, it also took about 50 minutes to reach the equilibrium exchange. When the solids content was increased further to 23 wt %, the time to achieve equilibrium exchange increased slightly to 70 minutes. Thus, these examples shows that equilibrium exchange can be achieved by increasing the solids content (i.e., using higher percent solids does not limit the equilibrium). However, as noted above, using greater than 20 wt % solids slightly extended the time to reach equilibrium, which would require increased residence time in the reactor. Advantageously, using 20 wt % solids equates to a 40% reduction in water used relative to the comparative example using 15% solids.

Figure 1:
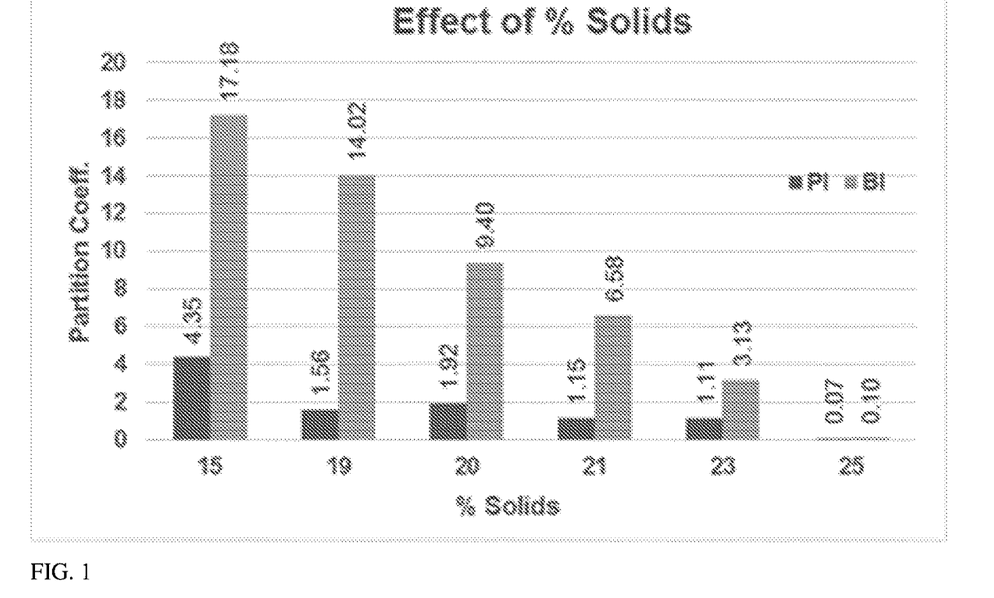
FIG. 1 shows the effect of solids content on the partition coefficient during extraction.

Partition coefficient experiments were carried out to further study the impact of higher percent solids. The term "partition coefficient" as used herein is defined as the ratio of the weight percent of a particular component in the organic phase to the weight percent of the same component in the aqueous phase. Partition coefficient experiments were carried out with an organic:aqueous ratio of 0.5:1 for up to 21 wt % solids content, and an organic:aqueous ratio of 1:1 for greater than 21 wt % solids content. The temperature was maintained at 120° C. Results are shown in FIG. 1, and indicate that the BI partition coefficient decreases with increasing the percent solids. Similarly phthalamide (PI) partition coefficient was also decreased with an increase in percent solids. The decrease in partition coefficient corresponds to the potential need for more stages for extraction or more solvent needed for the extraction.

Based on the experiments described above, the exchange reaction was carried out at pilot scale using 20 wt % solids. The aqueous reaction mixture having a solids content of 20 wt % and including the BI, PA, water and TEA in the amounts described above was heated in a vessel under pressure and agitated. The aqueous reaction mixture outlet of the reactor was fed into a 4 inch packed pilot extraction column to examine the effect of higher solids content on extraction efficiency and the overall yield of dianhydride (DA). The reactor outlet mixture was cooled and fed into the top of the first extraction column ("cold extraction column") where PI and BI were removed using toluene containing 5 wt. % triethylamine. The aqueous outlet of the first extraction column was preheated and fed to the second extraction column ("hot extraction column") to convert imide-anhydride intermediate (IA) to DA.

Table 1 below shows a summary of the cold extraction experiments carried out at the pilot scale at a temperature of 120° C. In Table 1, "Capacity" refers to the total flow into the column (e.g., flow of the combined aqueous and organic streams) per unit area, "Aqueous flow rate" refers to the rate at which the aqueous phase enters the column from the reactor. "Organic flow rate" refers to the rate at which the organic phase enters the column. "IA lost to back rxn" refers to the amount of the imide-anhydride species that is converted back to BI starting material, and then extracted into the organic phase and removed from the column. "IA lost to organic" refers to the amount of imide-anhydride species that is solubilized in the organic phase, and thus extracted from the column with phthalamide (PI) and bisimide (BI). "IA remaining in aq" refers to the amount of imide-anhydride species that remains in the IA form in the aqueous phase during the extraction. "BI extraction efficiency" and "PI extraction efficiency" refer to the percentage of BI and PI, respectively, that are removed with the toluene phase from the top of the column during the extraction, based on the inlet feed composition. It is noted that some small amount of BI or PI or both can remain in the aqueous phase. "IA to DA" refers to the conversion of the imide-anhydride species to the desired dianhydride tetra-acid salt.

TABLE 1

| Ex | Capacity (gph/sq. ft) | Aq. Flowrate (kg/hr) | Org. Flowrate (kg/hr) | Org:Aq (vol:vol) | IA lost to back rxn (mol %) | IA lost to organic (mol %) | IA remaining in aq (mol %) | IA to DA (mol %) | BI extraction efficiency (wt %) | PI extraction efficiency (wt %) |
|---|---|---|---|---|---|---|---|---|---|---|
| 1 | 500 | 106 | 53 | 0.5 | 10 | 4 | 87 | — | 94 | 90 |
| 2 | 500 | 83 | 71 | 1 | 8 | 6 | 78 | 7% | 93 | 96 |
| 3 | 500 | 66 | 85 | 1.5 | 7 | 9 | 77 | 7% | 94 | 97 |

The aqueous outlet of the cold extraction column was fed into the top of the hot extraction column to convert the IA to DA. Toluene was fed into the bottom of the column to remove residual PI and residual BI, which are formed during the conversion of IA to DA. Table 2 below shows the summary of the hot extraction experiments conducted at a temperature of 180° C.

TABLE 2

| Ex | Capacity (gph/sq ft) | Aq. Flowrate (kg/hr) | Org. Flowrate (kg/hr) | Temp. (° C.) | IA lost to organic (mol %) | IA lost to back rxn (mol %) | IA to DA (mol %) | IA remaining in aq (mol %) | IA relative to DA (wt. %) |
|---|---|---|---|---|---|---|---|---|---|
| 4 | 400 | 97 | 37.6 | 180 | 0.1 | 4 | 72 | 24 | 8 |
| 5 | 400 | 65 | 62 | 180 | 0.8 | 2 | 91 | 6 | 1.5 |

The inlet feed composition (i.e., the composition of the feed leaving the reactor and entering the cold extraction column) corresponded to the following molar fractions: 0.657 DA. 0.297 IA, and 0.046 BI. After conducting the cold and hot extractions in series, the overall yield of the desired DA was greater than 80%. For example, the overall DA yield can be calculated as 0.657 moles of DA+(0.297 moles IA*0.91 moles of IA converted to DA). Thus, the product stream of example 5 achieves 92.7% conversion to DA (0.657+(0.297*0.91)=0.927*100=92.7% DA at the end of the hot extraction). Thus the present inventors have shown that greater than 80% conversion to DA can be achieved at a solids content of 20 wt % and using a particular BI:PI molar ratio. Advantageously, the DA can have less than 2 wt % IA present.

In addition to solid content, other process parameters were also varied to determine their effect on the overall process yield. The following experiments were conducted at the pilot scale using a 4-inch diameter pilot extraction column. Trials were conducted such that the reaction was performed, and cold extraction was conducted. After conducting the cold extraction, the aqueous and organic phases were separated into two separate vessels. The aqueous phase was then fed to the hot extraction which was conducted with fresh toluene containing 5 wt % TEA.

Effect of Temperature

The following experiments were conducted to study the effect of cold extraction column operating temperature (i.e., the operating temperature of the first extractor). For these experiments, the reaction of BI with PA was conducted at a molar ratio of PA to BI of 5:1 at a temperature of 165° C. and at a pressure of 160 psig for 1 hour in the presence of a triethylamine exchange catalyst. The molar ratio of TEA to PA was 1.5:1. Percent solids was maintained in the range of 14 to 15 wt %. Water was used as the solvent for the reaction. The resulting aqueous reaction mixture was fed to the cold extraction column. Table 3 below summarizes the experimental results. Each of the parameters in Table 3 are as defined above for Tables 1 and 2.

including column configuration (e.g., column arrangement, flow of the organic solvent across the column, etc.).

Effect of Column Configuration

Two column configurations were examined: (1) parallel flow of organic solvent across the columns or (2) counter current flow of organic solvent across the columns. In the parallel flow configuration, the aqueous feed is provided to the top of each of the first (cold) and second (hot) extractors, toluene (containing TEA) is fed to the bottom of each of the first (cold) and second (hot) extractors, and the toluene fed to each extractor is fresh toluene. This arrangement can be seen in FIG. 2. In the countercurrent flow configuration, the aqueous feed is provided to the top of each of the first (cold) and second (hot) extractors, toluene (containing TEA) is fed to the bottom of each of the first (cold) and second (hot) extractors, and fresh toluene is fed to the second (hot) extractor, and the toluene removed from the top of the hot extractor is provided to the bottom of the first (cold) extractor. This arrangement is shown in FIG. 3.

In the following examples, toluene was used as the organic solvent. In the parallel flow column configuration, the ratio of the toluene feed rate to the aqueous stream feed rates was preselected such that it was effective for extraction of residual BI and residual PI. In the counter current flow column configuration, as described above, fresh toluene was fed to the hot extraction column, where residual PI and residual BI were extracted. The toluene containing the extracted PI and BI from the hot extraction column outlet was fed to the cold extraction column.

Table 4 shows the summary of cold extraction experiments conducted with different organic:aqueous ratios using the counter current flow configuration. The temperature at which the extraction was run in each of the following examples was 140° C. in the first extractor. In the counter

TABLE 3

| Ex. | Capacity (gph/sq. ft) | Aq. Flowrate (kg/hr) | Org. Flowrate (kg/hr) | Temp. (° C.) | IA lost to organic (mol %) | IA lost to back rxn (mol %) | IA to DA (mol %) | IA remaining in aq (mol %) |
|---|---|---|---|---|---|---|---|---|
| 6 | 500 | 105 | 44.5 | 140 | 6 | 14 | 21 | 59 |
| 7 | 500 | 111 | 45.9 | 160 | 5 | 34 | 7 | 54 |
| 8 | 500 | 112 | 44 | 150 | 9 | 22 | 23 | 46 |
| 9 | 400 | 66 | 54.7 | 120 | 13 | 5 | 16 | 66 |

The results shown in Table 3 indicate that the IA converted to BI and extracted into the organic phase (also referred to herein as "IA lost to reaction") increases with temperature. Specifically, a 10% increase in the amount of IA lost to reaction was observed for every 10° C. increase in temperature due to back reaction. Thus, the operating temperature for the cold extraction column was important in minimizing the amount of IA lost to back reaction.

In addition to temperature, several other parameters were also studied to understand the effect on IA back reaction, current flow configuration, the organic stream being removed from the hot extraction is fed to the cold extractor. Thus, the organic stream in the Table 4 examples includes the organic solvent (e.g., toluene) as well as PI, BI, and TEA in varying amounts, which are specified in the Table below as "Organic Stream Composition". Each of the remaining parameters in Table 4 are as defined above for Tables 1 and 2. "Capacity" refers to the total flow into the column (e.g., flow of the combined aqueous and organic streams) per unit area.

TABLE 4

| Ex | Capacity (gph/sq ft) | Aq. Flowrate (kg/hr) | Org. Flowrate (kg/hr) | Org. Stream Composition (wt %) | IA lost to Org. (mol %) | IA lost to back rxn (mol %) | IA to DA (mol %) | IA remaining in aq (mol %) | BI extraction efficiency (wt %) | PI extraction efficiency (wt %) |
|---|---|---|---|---|---|---|---|---|---|---|
| 10 | 400 | 86.1 | 41.8 | PI: 2.2%<br>BI: 1.3%<br>TEA: 5%<br>Toluene: 91.5% | 3 | 8 | 38 | 51 | 96.1 | 83 |

TABLE 4-continued

| Ex | Capacity (gph/sq ft) | Aq. Flowrate (kg/hr) | Org. Flowrate (kg/hr) | Org. Stream Composition (wt %) | IA lost to Org. (mol %) | IA lost to back rxn (mol %) | IA to DA (mol %) | IA remaining in aq (mol %) | BI extraction efficiency (wt %) | PI extraction efficiency (wt %) |
|---|---|---|---|---|---|---|---|---|---|---|
| 11 | 500 | 105 | 44.5 | PI: 4.4%<br>BI: 2.6%<br>TEA: 5%<br>Toluene: 88% | 6 | 14 | 21 | 59 | 91.3 | 67.7 |
| 12 | 500 | 95 | 51 | PI: 3.3%<br>BI: 1.95%<br>TEA: 5%<br>Toluene: 89.75% | 11 | 14 | 26 | 49 | 89.5 | 77.2 |

The results shown in Table 4 indicated that to minimize the amount of IA lost to back reaction and for better extraction of PI, toluene with a lesser concentration of PI is preferred (as in Example 10), which means indirectly higher amount of toluene to be fed into the hot column. The organic:aqueous of 1:1 in the countercurrent column configuration resulted in an organic stream having 2.2 wt % PI and 1.3 wt % BI, which enters cold column for extraction. Accordingly, an organic:aqueous solvent ratio of 1 may be advantageous for counter current flow configuration.

Table 5 shows the summary of cold extraction experiments conducted with varying organic:aqueous ratios using the parallel flow configuration. In the parallel flow configuration, fresh toluene (with 5 wt. % of TEA) was fed to both the cold and hot extractors. Each of the parameters in Table 5 are as defined above for Table 4.

wt %) do not significantly adversely affect the kinetics of the exchange reaction while also increasing the overall conversion to greater than 80%. In a further advantageous feature, the obtained dianhydride had less than 2 wt % IA present. The present inventors have found that using the increased solids content, which had not been demonstrated previously, provides a significant technical advantage in extraction processes, particularly where the amount of water used for the process can be reduced (e.g., a 40% reduction in water when a solids content of 20 wt % was used compared to 15 wt %). The present inventors have further advantageously found that two particular column configurations, described above and in FIGS. 2 and 3 (which have not been previously described), can be especially useful for conducting the extraction using two extractors as in the present disclosure.

TABLE 5

| Ex | Capacity (gph/sq ft) | Aq. Flowrate (kg/hr) | Org. Flowrate (kg/hr) | Temp. (° C.) | IA lost to Org. (mol %) | IA lost to back rxn (mol %) | IA to DA (mol %) | IA remaining in aq (mol %) | BI extraction efficiency (wt %) | PI extraction efficiency (wt %) | Org.:Aq. Ratio (v:v) |
|---|---|---|---|---|---|---|---|---|---|---|---|
| 13 | 400 | 90 | 42.5 | 120 | 4 | 7 | 9 | 79 | 96 | 97.4 | 0.5 |
| 14 | 400 | 65 | 57 | 120 | 1 | 6 | 25 | 67 | 95 | 97.1 | 1 |
| 15 | 400 | 95 | 31 | 120 | 8 | 7 | 8 | 76 | 91.1 | 92.7 | 0.33 |
| 16 | 500 | 103.2 | 50.6 | 120 | 6 | 4 | 13 | 76 | 96 | 95 | 0.5 |

As shown in Table 5, IA lost to back reaction (i.e., converted to bisimide) is 6 mol %. The results show that both BI and PI extraction efficiency significantly dropped with changing the organic:aqueous ratio. Accordingly, an organic:aqueous solvent ratio of at least 0.5 for each column can be advantageous for parallel flow configuration.

The aqueous outlet of the cold extraction column for the organic:aqueous ratios discussed above for each column configuration was fed into the hot extraction column to calculate the per pass yield of DA. Hot extraction trials consistently showed greater than 80% of IA can be converted to DA for both configurations, particularly when the organic:aqueous solvent ratios discussed above are employed.

International Publication No. WO 2017/189293 generally describes a method for producing an aromatic dianhydride which includes extracting the aqueous reaction mixture with an organic solvent for a first time and at a first temperature and subsequent to the first time, extracting the aqueous reaction mixture with an organic solvent for a second period of time at a second temperature. WO 2017/189293 does not address the effects of the solids content on extraction efficiency, and conducts extractions using an aqueous reaction mixture having a solids content of 16.4 wt %. In contrast, the present inventors have unexpectedly found that a higher solids contents (e.g., greater than 16.5 wt %, specifically 20

Thus, the process of the present disclosure provides a significant technical advantage over prior processes.

To further demonstrate the benefits provided by the present disclosure when using a two column extraction process as described herein, an additional comparative example was examined using an extraction with a single packed extraction column. The packing was GOODLOE packing. Reaction was carried out at a PA:BI molar ratio of 4.5:1 to 5:1 at a triethylamine TEA:PA molar ratio of 2:1. Solids content (% solids) was maintained in the range of 13 to 15%. The reaction was conducted at 170° C. at a pressure of 230 psig with a residence time of 1 hour. The aqueous feed was fed to the top of the packed extraction column, and toluene containing 5 weight percent (wt %) TEA was fed to the bottom of extraction column. The aqueous feed composition entering the extraction column was 45 mol % dianhydride as triethylammonium salts, 40 mol % IA as triethylammonium salts, and 15 mol % BI, all based on BI mole equivalents used in the reaction. Extraction was carried out with a temperature range of 145 to 170° C. with the pressure range of 200 to 250 psig. Results from three comparative examples are shown in Table 6 below. Table 6 shows the amount of IA lost to back reaction (33 to 45 mole percent) and the resulting average molar conversion of BI to DA (67 to 72%). As discussed above, the use of the present two column extraction process wherein a first extraction is conducted at lower temperature and a second extraction is conducted at higher temperature and the particular solids content discussed above resulted in 7 to 10 mole percent of IA lost to back reaction in the first extractor, and only an additional 2 to 4 mole percent of IA lost to back reaction in the second extractor. Molar conversions of BI to DA were greater than 80% (e.g., 87 to 93%). Without wishing to be bound by theory, it is believed that the differences between the inventive examples and comparative examples can, at least in part, be attributed to the extraction in the comparative examples being less efficient, causing more BI to be formed, which cannot be converted to DA. Thus, the increased conversion of IA to DA to the extraction process of the present disclosure is believed to be due to the increased extraction efficiency.

TABLE 6

| Comparative Example | Organic:Aqueous ratio (Vol) | Maximum capacity (gph/Sq. ft) | Minimum capacity (gph/sq. ft) | IA lost to back rxn (mol %) | BI to DA Conversion (mol %) | IA relative DA (wt %) |
|---|---|---|---|---|---|---|
| C1 | 1.4 | 361.26 | 177.24 | 33 | 72 | 2.5 |
| C2 | 1.2 | 358.02 | 155.1 | 38 | 70 | 2.5 to 3 |
| C3 | 1 | 325.44 | 141 | 45 | 67 | 2.5 to 3 |

This disclosure further encompasses the following aspects.

Aspect 1: A method for producing an aromatic dianhydride, the method comprising reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 150 to 300 psig, preferably 200 to 250 psig; removing the N-substituted phthalimide from the aqueous reaction mixture by extracting the aqueous reaction mixture with an organic solvent in a first extractor, for a first time period, at a first extraction temperature that is 60 to 160° C., provided that the first extraction temperature is at least 10° C., preferably at least 20° C. or more preferably at least 30° C., or most preferably at least 40° C. lower than a maximum of the reaction temperature; subsequent to the first time period, extracting the aqueous reaction mixture with an organic solvent in a second extractor, for a second time period, at a second extraction temperature that is 120 to 250° C., provided that the second extraction temperature is at least 5° C., preferably at least 10° C., more preferably at least 20° C. higher than the first extraction temperature; and converting the aromatic tetraacid salt to the corresponding aromatic dianhydride; wherein the aqueous reaction mixture has a solids content of greater than 16.5 wt %; and wherein extracting in the first extractor and the second extractor uses a column configuration wherein the organic solvent provided to the first extractor and the second extractor simultaneously is fresh organic solvent and the organic solvent is provided to the first and second extractors in a volumetric ratio of the organic solvent to the aqueous medium is greater than or equal to 0.5:1; or the organic solvent provided to the second extractor is fresh organic solvent and the organic solvent from the second extractor is fed to the first extractor and the organic solvent is provided to the second extractor in a volumetric ratio of the organic solvent to the aqueous medium is 0.5:1 to 1.5:1.

Aspect 2: The method of aspect 1, wherein the first extractor and the second extractor are configured such that the organic solvent is fresh organic solvent provided to the first extractor and the second extractor simultaneously and the organic solvent is provided to the first and second extractors in a volumetric ratio of the organic solvent to the aqueous medium is greater than or equal to 0.5:1.

Aspect 3: The method of aspect 1, wherein the first extractor and the second extractor are configured such that the organic solvent provided to the second extractor is fresh organic solvent and the organic solvent from the second extractor is fed to the first extractor and the organic solvent is provided to the second extractor in a volumetric ratio of the organic solvent to the aqueous medium is 0.5:1 to 1.5:1.

Aspect 4: The method of any one or more of aspects 1 to 3, wherein the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing, preferably phthalic anhydride; and the exchange catalyst comprises a ($C_{1-20}$ alkyl)-substituted amine, preferably a tri($C_{1-20}$ alkyl)amine, more preferably triethylamine, trimethylamine, or a combination comprising at least one of the foregoing.

Aspect 5: The method of any one or more of aspects 1 to 4, wherein the initial molar ratio of phthalic anhydride to aromatic diimide is 4:1 to 20:1, or 4:1 to 10:1, or 4:1 to 8:1, or 4:1 to 5.5:1 and the initial molar ratio of amine exchange catalyst to the phthalic anhydride is 1:1 to 2:1.

Aspect 6: The method of any one or more of aspects 1 to 5 wherein the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; and the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing.

Aspect 7: The method of any one or more of aspects 1 to 6, wherein the organic solvent comprises toluene, xylene, chlorobenzene, ortho-dichlorobenzene, or a combination comprising at least one of the foregoing, and optionally wherein the organic solvent further comprises 0 to 15 weight percent of a tri($C_{1-6}$ alkyl) amine), preferably triethylamine.

Aspect 8: The method of claim 1, wherein the volumetric ratio of the organic solvent to aqueous medium is 0.3:1 to 3:1.

Aspect 9: The method of any one or more of aspects 1 to 8, wherein conversion of the aromatic diimide to the aromatic dianhydride is greater than 70%, or greater than 75%, or greater than 78%, or greater than 80% at the end of the second time period.

Aspect 10: The method of any one or more of aspects 1 to 9, wherein the method is a batchwise method or a continuous method.

Aspect 11: The method of any one or more of aspects 1 to 10, wherein the reaction temperature is 160 to 200° C.; the first extraction temperature is 60 to 150° C.; and the second extraction temperature is 140 to 250° C.

Aspect 12: An aromatic dianhydride prepared by the method of any one or more of aspects 1 to 11, wherein the aromatic dianhydride has an imide anhydride content of 2 weight percent or less.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another.

The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some aspects", "an aspect", and so forth, means that a particular element described in connection with the aspect is included in at least one aspect described herein, and may or may not be present in other aspects. In addition, it is to be understood that the described elements may be combined in any suitable manner in the various aspects.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references, including priority European patent application no. 18172207.5 filed May 14, 2018, are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl) a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{6-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for producing an aromatic dianhydride, the method comprising
reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 150 to 300 psig (1.13 to 2.16 MPa);

removing the N-substituted phthalimide from the aqueous reaction mixture by extracting the aqueous reaction mixture with an organic solvent in a first extractor, for a first time period, at a first extraction temperature that is 60 to 160° C., provided that the first extraction temperature is at least 10° C. lower than a maximum of the reaction temperature;

subsequent to the first time period, extracting the aqueous reaction mixture with an organic solvent in a second extractor, for a second time period, at a second extraction temperature that is 120 to 250° C., provided that the second extraction temperature is at least 5° C. higher than the first extraction temperature; and converting the aromatic tetraacid salt to the corresponding aromatic dianhydride;

wherein the aqueous reaction mixture has a solids content of greater than 16.5 weight percent; and wherein extracting in the first extractor and the second extractor uses a column configuration wherein
the organic solvent provided to the first extractor and the second extractor simultaneously is fresh organic solvent and the organic solvent is provided to the first and second extractors in a volumetric ratio of the organic solvent to the aqueous medium is greater than or equal to 0.5:1; or
the organic solvent provided to the second extractor is fresh organic solvent and the organic solvent from the second extractor is fed to the first extractor and the organic solvent is provided to the second extractor in a volumetric ratio of the organic solvent to the aqueous medium is 0.5:1 to 1.5:1.

2. The method of claim 1, wherein the first extractor and the second extractor are configured such that the organic solvent is fresh organic solvent provided to the first extractor and the second extractor simultaneously and the organic solvent is provided to the first and second extractors in a volumetric ratio of the organic solvent to the aqueous medium is greater than or equal to 0.5:1.

3. The method of claim 1, wherein the first extractor and the second extractor are configured such that the organic solvent provided to the second extractor is fresh organic solvent and the organic solvent from the second extractor is fed to the first extractor and the organic solvent is provided to the second extractor in a volumetric ratio of the organic solvent to the aqueous medium is 0.5:1 to 1.5:1.

4. The method of claim 1, wherein
the substituted or unsubstituted phthalic anhydride is phthalic anhydride, 3-halophthalic anhydride, 4-halophthalic anhydride, 3-nitrophthalic anhydride, 4-nitrophthalic anhydride, or a combination comprising at least one of the foregoing; and
the exchange catalyst is a $(C_{1-20}$ alkyl)-substituted amine.

5. The method of claim 1, wherein the initial molar ratio of phthalic anhydride to aromatic diimide is 4:1 to 20:1 and the initial molar ratio of amine exchange catalyst to the phthalic anhydride is 1:1 to 2:1.

6. The method of claim 1 wherein
the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; and
the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing.

7. The method of claim 1, wherein the organic solvent is toluene, xylene, chlorobenzene, ortho-dichlorobenzene, or a combination comprising at least one of the foregoing.

8. The method of claim 1, wherein the volumetric ratio of the organic solvent to aqueous medium is 0.3:1 to 3:1.

9. The method of claim 1, wherein conversion of the aromatic diimide to the aromatic dianhydride is greater than 70% at the end of the second time period.

10. The method of claim 1, wherein the method is a batchwise method or a continuous method.

11. The method of claim 1, wherein
the reaction temperature is 160 to 200° C.;
the first extraction temperature is 60 to 150° C.; and
the second extraction temperature is 140 to 250° C.

* * * * *